United States Patent [19]

Lin

[11] 4,443,851
[45] Apr. 17, 1984

[54] AUTOMATIC RECORDING, INDICATING AND PREDICTING DEVICE FOR GYNECOPHYSIOLOGICAL CYCLES

[76] Inventor: Kin-Yuan Lin, 14, Nung 33, Lane 269, Li Shan St., Nei Hu, Taipei, Taiwan

[21] Appl. No.: 403,037

[22] Filed: Jul. 29, 1982

Related U.S. Application Data

[63] Continuation of Ser. No. 165,807, Jul. 3, 1980, abandoned.

[51] Int. Cl.³ .............................................. A61B 5/04
[52] U.S. Cl. .................................. 364/415; 128/738; 340/711; 374/102; 374/186
[58] Field of Search ...................... 364/413, 415, 710; 128/734–738; 340/525, 711, 722, 752, 753, 784, 789; 73/343 R, 344, 339 R, 343.5

[56] References Cited

U.S. PATENT DOCUMENTS

| | | | |
|---|---|---|---|
| 3,968,499 | 7/1976 | Lowe et al. | 340/722 |
| 4,031,365 | 6/1977 | Raggiotti et al. | 364/557 |
| 4,038,668 | 7/1977 | Quarton | 340/722 |
| 4,127,848 | 11/1978 | Shanks | 340/784 |
| 4,148,304 | 4/1979 | Mull | 128/738 |
| 4,151,831 | 5/1979 | Lester | 364/415 |
| 4,193,122 | 3/1980 | Bowers | 340/722 |
| 4,216,471 | 8/1980 | Akred, Sr. | 340/752 |
| 4,246,907 | 1/1981 | Bullock | 128/738 |

Primary Examiner—Errol A. Krass
Attorney, Agent, or Firm—Armstrong, Nikaido, Marmelstein & Kubovcik

[57] ABSTRACT

The present invention relates to a microprocessing device which detects, records, analyzes and plots the basal body temperature change in conjunction with calendar rhythmic method through measuring, recording and storing the data of the continuously changing body temperature and the period of duration of a plurality of cycles to set the (birth of babies) under the users' control, and it may act as a digital calender clock with musical alarm device when not used for the aforesaid purposes.

1 Claim, 6 Drawing Figures

AUTOMATIC RECORDING, INDICATING AND PREDICTING DEVICE FOR GYNECOPHYSIOLOGICAL CYCLES

This is a continuation of application Ser. No. 165,807, filed July 3, 1980 now abandoned.

BACKGROUND OF THIS INVENTION

Figure 1:
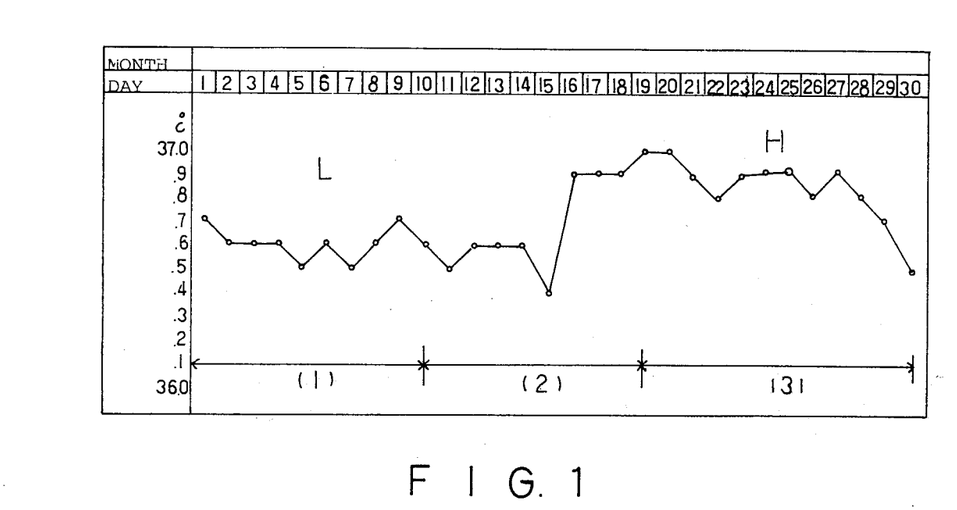
FIG. 1 is a BBT curve revealing the biphase curve of the BBT of normal women plotted on a temperature (in Celsius degree) versus time (in days) coordinate.

According to the recent gynecophysiological research and the results of practical application thereof, the basal body temperature (hereinafter referred to as BBT) method has been verified to be by far one of the most effective ways of birth control, and it is also the only allowable way of contraception for Catholics. The term BBT method, as its name implies, refers to the method involving ascertaining the date of ovulation by virtue of a series of observation of the biphasic change of body temperature. FIG. 1 shows a one-month period of a menstral cycle to find the proper period of intercourse, so as to avoid, or in the opposite sense, if any, to cause pregnancy depending on the users' preference, in other words, to become pregnant under control.

Nevertheless, it was still found difficult to put such an ideal method into extensive practice by known means in an easy, convenient way since in order to obtain a reliable curve describing the cyclic change of body temperature, frequent measurements are required to record the continuously changing body temperature to get enough "samples" to sketch a graph with the requisite reliability, therefore taking much time. Moreover, it suffers such disadvantages as the inaccuracy of the data obtained, the trouble in recording, and the tendency of forgetting the daily measurement. Besides, graphical method fails to provide useful information of the pre-ovulation safe period, i.e., it is only cabable of ascertaining the ovulation date thereafter, but unable to predict it beforehand.

Accordingly, it is the main object of the present invention to obviate and mitigate the existing defects of birth control using the BBT method, which, although appears to be effective, has seldom been practically accepted due to the foregoing technical problems thereof.

SUMMARY

The present invention relates to an instrument detecting, recording, analyzing and plotting the basal body temperature change curve of women and more particularly, to one that takes advantage of the fluctuation of the basal body temperature and the period of duration corresponding to the women's cyclically physiological change, thereby predicting the date of the coming ovulation, to control the birth. It is directed to overcome the existing difficulties and disadvantages of the conventional methods, and is characterized by the features and advantages listed as follows:

1. To most women with normal menstruation, this invention is capable of predicting their possible period of gestation of the next menstrual cycle after a period of applying this invention by combining Ogino's Method (also referred to as "Calendar Rhythmic Method"), a method inferring the safe period in between two successive menstruations, and the data processing and memorizing capacity of micro-computer, to exhibit specified signals on the liquid crystal display (hereinafter referred to as LCD display), to arouse the attention of the users to make precautionary disposal.
2. By means of a thermistor and a bridge circuit, then through an analog-digital converter with high sensitivity, this invention feeds the information of body temperature into the main section of the micro-computer, thereby performing such tasks as autozero, finding the mean value, and the choice and interconversion between Celsius and Fahrenheit degree.
3. The present invention can plot the BBT curve from the beginning of a cycle to the day of measurement by a continuous curve rather than a group of scattered points by virtue of the data processing capacity of the micro-computer in conjunction with LCD display and the driving circuit thereof.
4. In case any abnormal condition which may appreciably affects the body temperature, for example, a fever or other factors, occurs in the very date of measurement, the information may be fed through pressing the keyboard to instruct the micro-computer to "label" the position designating the suffering date on the LCD display automatically to avoid misjudgment from the erroneous information of the abnormal curve afterwards.
5. In order to awaken the sleeping user in an easy and unstrained manner, to make the daily measurement without distrubing the essential basal condition required in BBT method, this invention is provided with a musical alarm means which produces a harmonious melody at a pleasing level when the preset time is reached.
6. This invention is provided with an automatic electronic calender clock which may date to as late as 2000 A.D.
7. Owing to the relatively small size of this invention it is power-saving and thus can be designed as portable for convenience and carrying. To avoid the possible troubles due to power shortage or the depletion of power source this invention is preferably equipped with a reminding means which reminds the user to recharge the power source when the stored power fails below a predetermined level.

In view of the foregoing advantages, it is fair to say that the present invention is indeed to accomplish a revolutionizing improvement in overcoming the incovenience and disadvantages of the conventional means of controlling birth based upon BBT method, especially in its function of predicting the possible period of gestation which cooperates with the continuously changing BBT curve revealed on the liquid crystal display which greatly facilitates its operation and makes both contraception and pregnancy fairly easy-depending on the users will.

Numerous other features, objects, and advantages of the invention will become apparent from the following specification when read in connection with the accompanying drawing in which:

DETAILED DESCRIPTION OF PREFERRED EMBODIMENTS

With reference now to the drawing and more particularly FIG. 1 thereof, there is shown a graphical representation of a cycle of the biphasic BBT curve of normal women, which bi-phasic curve includes two phases repectively designated by L, the former half of a period, namely a low-temperature phase; and H, the latter half of a period, namely a high-temperature phase. Also, the cycle can be divided, according to the possibility of pregnancy, into three stages: Early stage (1), (or preovulation safety stage), middle stage (2) (the possible stage of pregnancy, wherein the day designated by the abruptly sharp increase following a decreasing curve is the date of ovulation), and late stage (3) (or post-ovulation safety stage).

Figure 2:
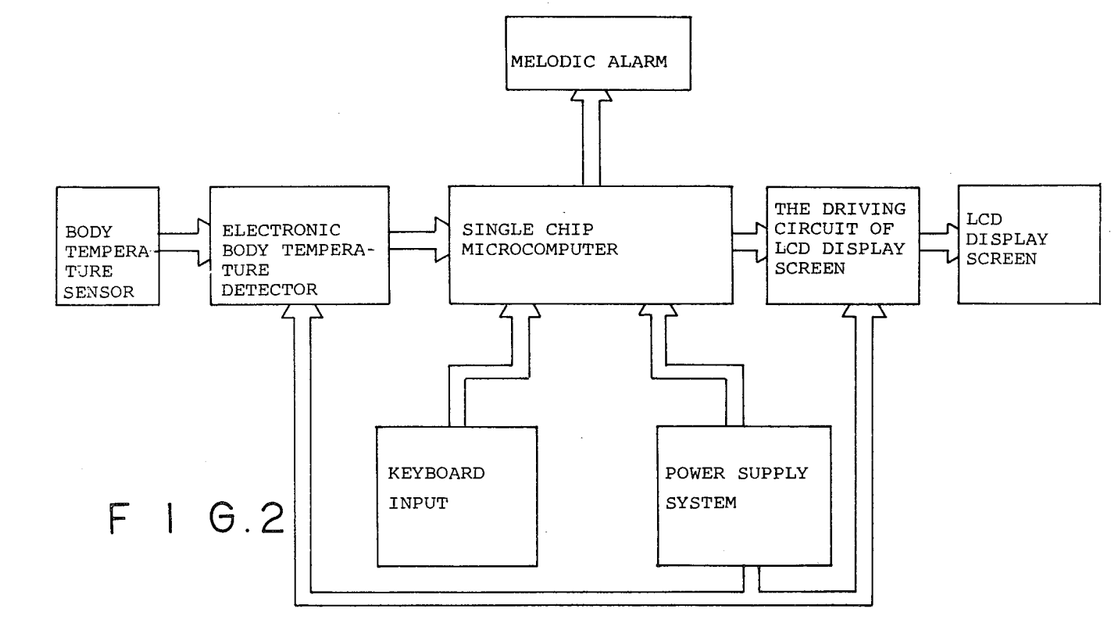
FIG. 2 is the overall block diagram illustrating the logical arrangement of the device according to the present invention.

Structurally, the present invention comprises:

(1) a single chip micro-computer containing a microprocessor and memories, a peripheral devices including and electronic body temperature detector with an analog-digital convertor, a keyboard for data entry, a LCD display with a dot matrix and seven segment portions, and the driving circuit thereof, and a melody generator etc.;

(2) a power supply system consisting of a charging device, rechargeable batteries, and a reminding device for recharging controlled by software program. The complete system block diagram is shown in FIG. 2, which is is described in detail hereafter:

(1) Single Chip Microcomputer and Its Peripheral Devices

Figure 3:
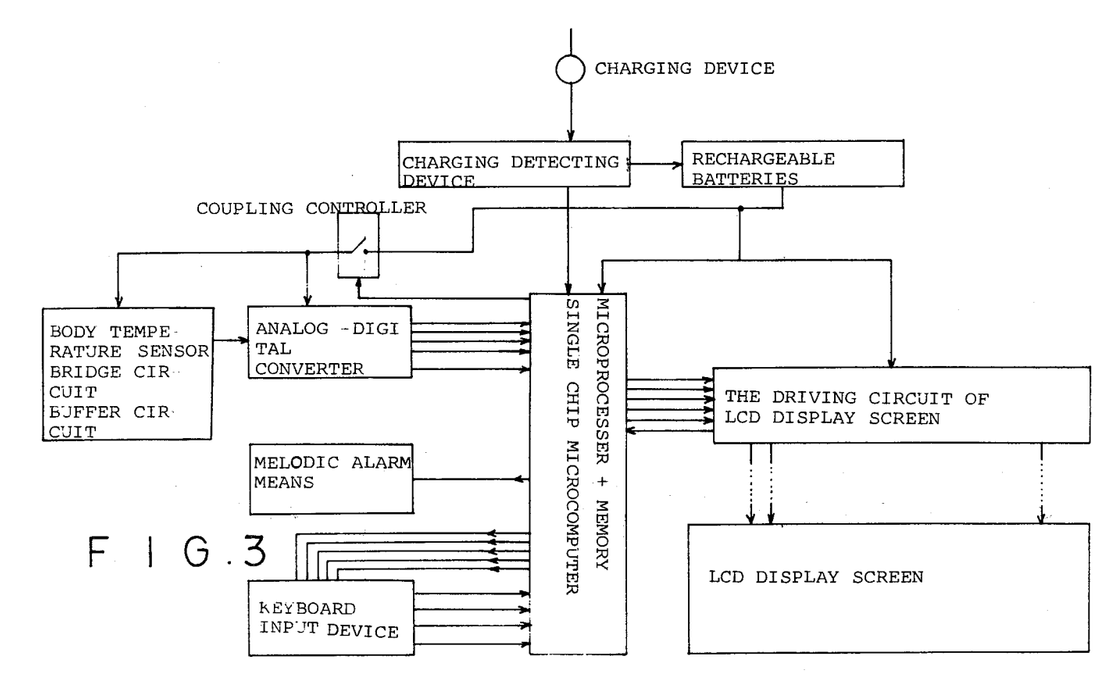
FIG. 3 is a more detailed block diagram illustrating the logical arrangement according to the present invention.

This section employs a single chip micro-computer with low power consumption as the memory and processing unit for data, and employs the input keyboard (which will be mentioned about hereafter in (1a)) and the electronic body temperature detector (which will be mentioned about in (1b) hereafter) for inputting data and the dot matrix digital LCD display the driving circuit thereof (see (1c) hereafter) and a melodic alarm means as the output of data as its peripheral devices. FIG. 3 is the block diagram of the circuit, which, when not used to measure the body temperature, functions as an electronic calender clock by displaying the information about what year, mouth, day, hour and minute it is. However, the clock becomes a processing unit for the data for body temperature when the preset time is reached, to process the data corresponding to the body temperature obtained from the electronic body temperature detector every day, and plot the graph of update BBT changes of that period using a continuous curve on the LCD display screen. Additionally, the melodic alarm means may awake the user in an easy and unstrained manner by beautiful, soft music to start the daily measurement of body temperature a the preset time which is generally set in the last night as the time the user desires to wake up next morning.

(a) Keyboard for information input

The keyboard comprises ten numerical keys from 0 to 9 and ten functional keys, namely, STR, DSP, CLR, MEA, DAT, AL, CLK, FD, GRA, ERR, in which the ten numerical keys and STR, DAT, CLK, AL, FD, are used in the input of the date, the time, the time to get up and the first day of a cycle respectively, while DSP cooperates with DAT, CLK, AL, FD, and GRA, together to reveal the date, time, waking time, the first day of a cycle and the starting point of the changing curve (starting date) on the LCD display. STR, together with ERR, works as the input under abnormal conditions, e.g. having a fever, STR and MEA, on the other hand, combine to carry out the measurement, the memorizing, and the data processing of body temperature. If MEA works solely, it merely acts as the measurement of body temperature. CLR is used to clear the LCD display provided any error occurs during operation, or wrong information is inadvertently fed into the machine.

(b) Electronic body temperature detector

Figure 4:
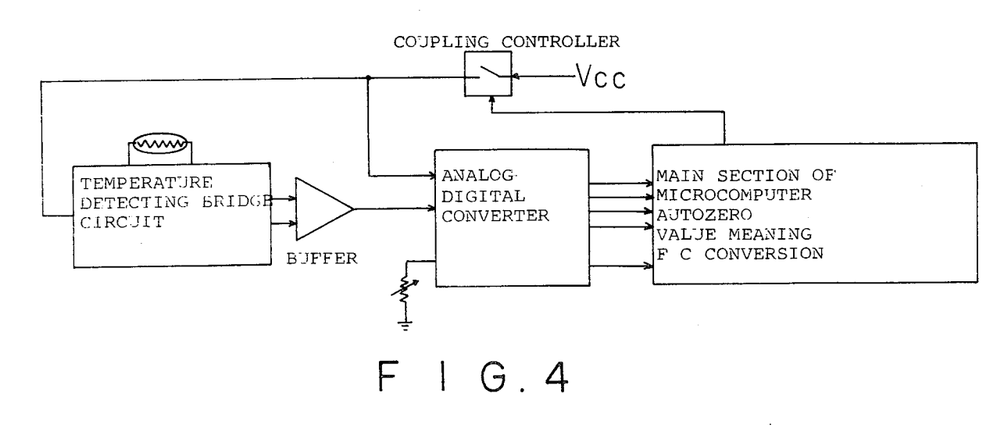
FIG. 4 is a block diagram of the electronic temperature measuring device.

This device uses a medical thermistor as the sensor of body temperature. A signal of body temperature is transferred to an analog-digital converter via a bridge circuit and a buffer. The analog-digital converter has a resolution of 1 milivolt. The body temperature detector can reduce the self-heated effect of the thermistor by means of a coupled controller to enhance the accuracy of this device. The autozero, the finding of a mean valne, and the conversion of C.°–F.° are accomplished by a software program. A more detailed circuit block diagram is shown in FIG. 4.

(c) Liquid Crystal display and its driving circuit

Figure 5:
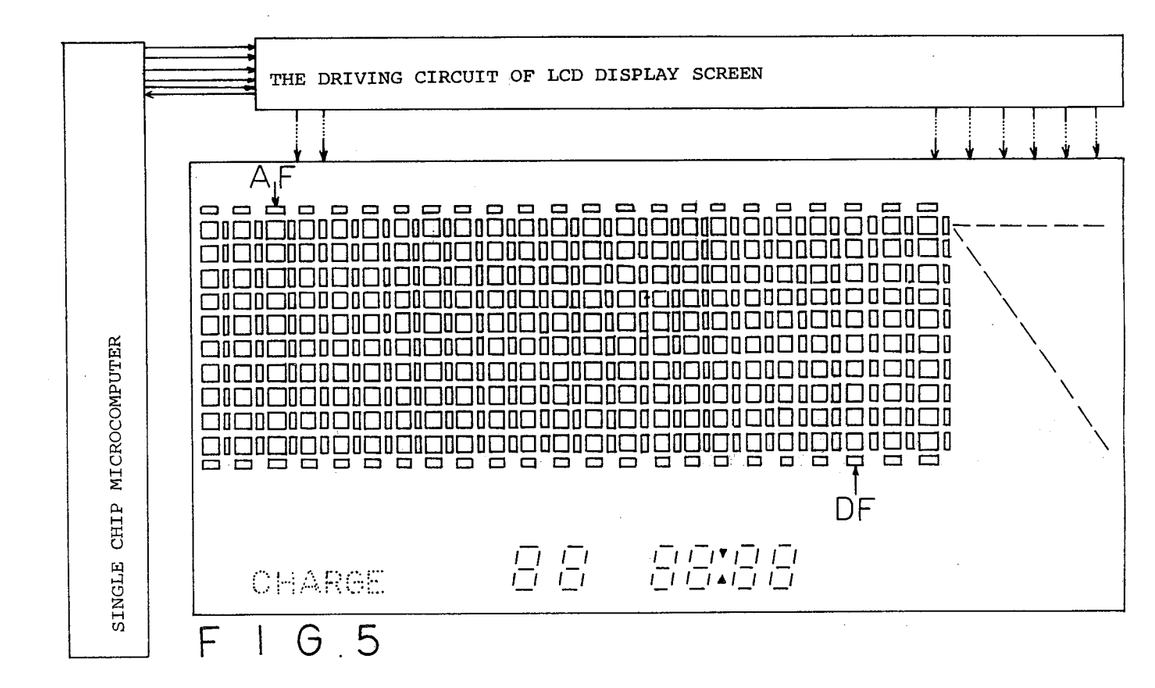
FIG. 5 and FIG. 6 are the enlarged graphical representation of the LCD display screen of dot matrix and the seven segment LCD display.

The multiplex LCD display comprises a dot matrix describing the BBT curve, a seven-segment digital display which indicates the date, moment, temperature, and a reminding signal of recharging. Referring to FIG. 5, the signal sent out by the microcomputer, after having entered the driving circuit with both encoding and decoding functions, produces the signal and voltage waveform required to drive the multiplex display, thereby describing the desired pattern and digits on the display. The abscissa of the dot matrix of the LCD display indicates the date, whereas the ordinate thereof, the temperature. The date of the abscissa axis is linked with the date shown on the digital display through a date flag DF (see FIG. 6), i.e. the date represented by the alsciscsa of the position where the date flag is seated is the very data of the date that appears on the digital display. The uppermost row of the dot matrix, on the other hand, functions under abnormal condition, wherefrom the user can read the date of such abnormality.

Figure 6:
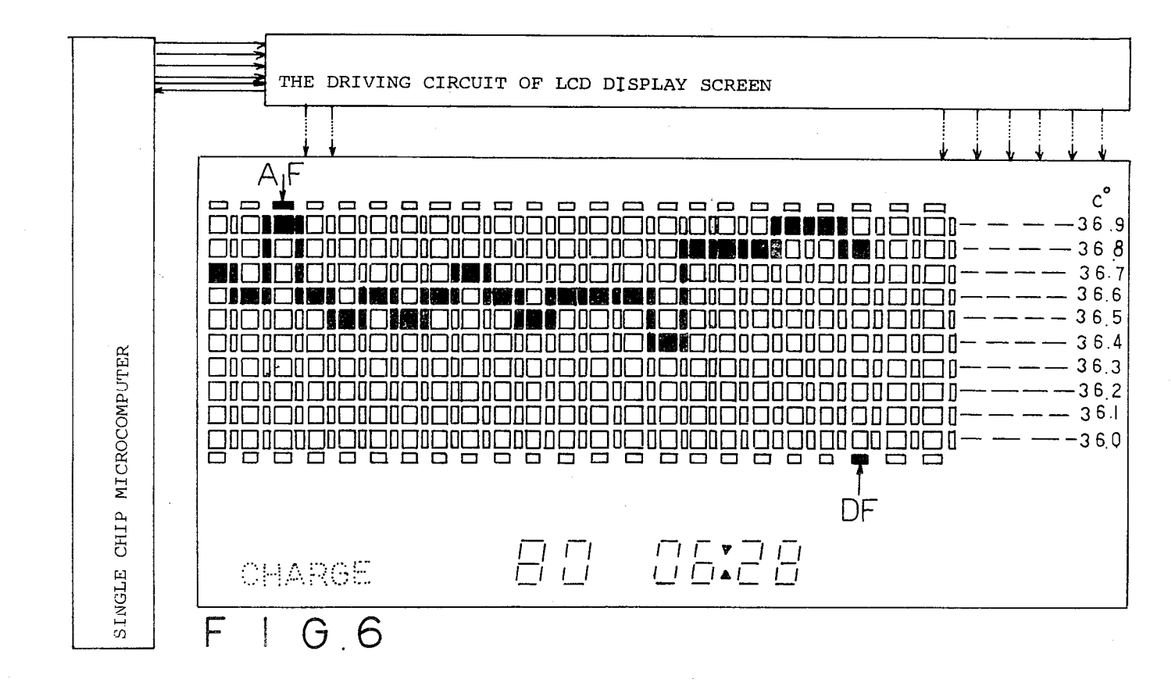

Each column of the dot matrix includes a line of coarse, square dots and a line of fine, narrow dots, wherein the square dots designate the BBT data, while the narrow dots act as the interconnection between two adjacent square dots to link the train of scattered points together so as to form a nearly continuous curve rather than a series of independent points, thus offering the plot such advantages as clearness and easiness to discern. Referring to FIG. 6 suppose all the BBT data from the first day of a given period, say June 8, 1980 to the day of detection, June 28, 1980 for example, are all revealed on the LCD dot matrix screen, and the position where the date flag DF occurs indicates the abscissa of the point on the curve showing the body temperature of the date wherein the body temperature is measured. Note the abnormality flag AF appearing in the position of June 10 indicates that the body temperature was measured under abnormal condition in that day. It must be pointed out that the plot in FIG. 6 appears more or less unsmooth and discontinuous because it is magnified, nevertheless in actual use the plot may appear fairly smooth and nearly continuous by photographical reduction technique.

(d) Melodic alarm device

The unit operates to awake the user in an easy unstrained manner so as not to disturb or interfere the basal condition which is essential to the measurement of BBT by producing charming music via the micro-computer by means of software and hardware (melody generator).

(2) Power Supply System

The power supply system according to the present invention, as shown in FIG. 3, comprises a charging detector, rechargeable batteries, a reminder program and signal indicating recharging is necessary, and a charging device.

Inasmuch as the invention needs to receive new information of BBT constantly for data recording and processing, no power cut is allowed. In order to prevent that, the charging detector inputs a signal to instruct the microcomputer when the cell is being charged, to remind the user to recharge by the flashing a sign "CHARGE" on the LCD display by means of the charging reminding program after a definite time from the last charging, the duration of which is preset depending on the capacity of the rechargeable batteries.

(3) Operating Instruction (a) After having been switched on, a series of figures comprising exclusively zeroes, "00 0000" appears on the 7-segment LCD display immediately, yet nothing occurs on the corresponding displaying screen of dot matrix. Then the corresponding keys on the keyboard representing the present date are pressed, for example, 8, 0, 0, 5, 1, 5, if it is May 15, 1980, then the functional key STR and DAT are pressed. In this way, the information of date is fed into the micro-computer. Then the corresponding keys representing the hour and minute at that moment are pressed, and subsequently, the STR, and CLK are pressed and the information of hour and minute thus enters the microcomputer. Now the indicator becomes an electric calender clock dating to as late as 2000 A.D. in which all the possible irregular cases, say the occurrence of leap years within common years, or the althernating 30-day months and 31-day months, and Februarys, are taken into account. Hence, the user can find correct desired information of dates whenever it is needed by pressing the DSP and DAT to reveal the date on the seven-segment display. Likewise, by pressing DSP and CLK the user can read the data of day, hour, and minute from the display.

(b) Measurement of BBT

Having thus finished the operation according to the operating instruction of 3(a), the user only need wait for the coming of the first day of next cycle, on which day the date can be shown on the display by feeding the information and corresponding instruction of the first day into the microcomputer. Meanwhile the microcomputer clears the BBT data of the perceding month, but stores the data pertaining to the duration of the cycle thereof so as to predict the next period in which pregnancy is possible. After the aforementioned preparatory work is finished, the waking time of the morning on the date of measurement is preset one day therebefore, (Preferably, BBT is measured prior to any activity of the body in the morning after waking up. If the user can get up in time and remember to make measurement without the aid of any alarm means, the presetting of a time can be omitted) so that the melodic alarm device may give euphonic music by that time to awaken the user in an easy and unstrained manner to proceed with the measurement. The corresponding numerical keys are pressed to set the desired waking time, followed by the STR and AL. As a result, the set-time appears on the digital display. For example, if the user intends to get up on 6:30 a.m. in the next morning, he may press the keyboard according to the order: 0, 6, 3, 0, STR and AL. A Combined sign, both digital and alphabetical, AL 06 30 thus appears on the digital display, and a musical sound will be produced at 6:30 in the next morning. The next step is the daily taking of the BBT measurement which is the same for every day. The first operation after waking up in the morning everyday is to measure the body temperature by first pressing CLR to stop the music, and next placing the temperature sensor into a proper portion of the body (the month or the ears, for example) to measure the body temperature, then pressing the STR and MEA. After 30 to 40 seconds or so the device will give a signal sound, and simultaneously the information of the body temperature will appear on the display, the appearance of which indicates that the measurement is complete. Then the corresponding data will produce a dot on the LCD displaying screen of the dot matrix, and the date flag appears in the bottommost row thereof. Heretofore the microcomputer has finished the sequence of operations including measurement, recording, memorizing and displaying. Provided the user has continuously used the detector for a definite time, (generally half a year, however the longer is the time, the more reliable the result will be), the micro-computer will predict the possible period of pregnancy of a beginning cycle, and add to the position of the date a twinkling date flag to caution the user. However to those users with unstable or irregular period, the invention does not make any prediction to avoid misjudgement.

(c) Other functions

In case the user desires to read the curve beginning with an appointed day (i.e. any of the past days) he may first press the keys of the corresponding month and day, and next press the DSP and GRA, then he will see the corresponding curve of that date appearing on the leftmost coordinate. Such function is very useful to those women having longer menstrual cycles since the scale for the displaying screen is not long enough to display the complete longer cycle. Fruther, in case the user finds some unusual condition which may probably affect the body temperature while making measurement, he must instruct and communicate with the microcomputer by pressing the digital keys corresponding to the month and day, then the STR and ERR. In so doing, an indicating flag of abnormal condition will appear in the position corresponding to that date, the information of which is thus stored in the memory for the judgement afterwards.

The novelty, features, and operating instruction of my invention have thus been disclosed hereinbefore. It is evident that those skilled in this art may now make numerous uses and modifications of the specific embodiments described herein without departures from the specific inventive concepts. Consequently, this invention is to be construed as embracing each and every novel feature and novel combination of features present in or possessed by the apparatus and techniques herein disclosed and limited solely by the spirit and scope of the appended claims.

What I claim:

1. A device for analyzing menstrual cycles comprising:
   (a) a sensor means for sensing body temperature;
   (b) keyboard input means for providing input data representative of the date, time, start of prior menstrual cycles and abnormal body conditions;
   (c) microprocessor means having data processing and storage means including memory storage means for storing data representative of body temperature, including abnormal conditions during the previous days in a current menstrual cycle, and data representative of the first day of at least one prior menstrual cycle;
   said data processing and storage means also including calendar means for providing calendar data, including at least data representative of the actual date and the safe period between two successive menstruations, for providing a continuous curve of body temperature versus date to provide an indication of the anticipated start of ovulation prior to the start thereof while, in the case of any abnormal condition that may appreciably affect the body temperature, comprising fever factors that occur during the sensing of the body temperature, data representative of any said abnormal condition is fed through the keyboard to instruct the microprocessor to label the date automatically and, in so doing, to provide an indicating flag of abnormal conditions that will correspond to the date thereof;
   said microprocessor means also coupled to said sensor and said keyboard means for receiving inputs therefrom and for processing said inputs to provide output data representative of body temperature as a function of date, whereby said device predicts the period of gestation and next menstrual cycle for women, including women having long menstrual cycles, as a function of said calendar data, said body temperature and said first day of at least one prior menstrual cycle;
   (d) graphic display means having flag means coupled to said keyboard input means by said microprocessor means for receiving data and displaying said data in a continuous curve of body temperature versus date to provide an indication of the same, the abnormal conditions and the anticipated start of ovulation prior to the start thereof, the graphic display means becoming operative to indicate an abnormal condition on a specific date when instructed to do so by data input at the keyboard, whereby said device detects, records, analyzes and plots body temperature change and abnormal conditions in conjunction with a rhythmic method for measuring, recording and storing the data of the continuously changing body temperature for providing an automatic recording, indicating and predicting device for gynecophysiological cycles.

* * * * *